United States Patent [19]

Bloch

[11] 3,939,197

[45] Feb. 17, 1976

[54] PROCESS FOR THE PREPARATION OF ALKALINE SULFATE ESTERS OF N-ALKYL-SUBSTITUTED HYDROXYPOLYALKOXYMETHYLCYCLOHEXENES

[75] Inventor: Herman S. Bloch, Skokie, Ill.
[73] Assignee: Universal Oil Products Company, Des Plaines, Ill.
[22] Filed: Nov. 4, 1974
[21] Appl. No.: 520,693

Related U.S. Application Data

[63] Continuation-in-part of Ser. No. 277,835, Aug. 3, 1972, Pat. No. 3,859,324.

[52] U.S. Cl. .............................................. 260/458
[51] Int. Cl.² ....................................... C07C 141/12
[58] Field of Search .... 260/457, 458, 611 B, 617 R, 260/631 R

[56] References Cited
UNITED STATES PATENTS

| | | | |
|---|---|---|---|
| 2,174,131 | 9/1939 | Lubs | 260/457 |
| 2,236,919 | 4/1941 | Reynhart | 260/611 B |
| 2,318,296 | 5/1943 | Dickey | 260/457 |
| 2,435,403 | 2/1948 | Morris et al. | 260/617 R |
| 2,496,582 | 2/1950 | Enyeart | 260/611 B |
| 2,863,925 | 12/1958 | Starcher | 260/617 R |
| 3,832,408 | 8/1974 | Anderson | 260/458 |

OTHER PUBLICATIONS

Alder et al., Berichte, 71, pp. 1939–1957, (1938).

Primary Examiner—James O. Thomas, Jr.
Assistant Examiner—Nicky Chan
Attorney, Agent, or Firm—James R. Hoatson, Jr.; Raymond H. Nelson; William H. Page, II

[57] ABSTRACT

Anionic biodegradable detergents as exemplified by alkaline sulfate esters of n-alkyl-substituted hydroxypolyalkoxymethylcyclohexenes may be prepared by condensing butadiene with allyl alcohol, ring alkylating the resultant hydroxymethylcyclohexene with an olefin in the presence of a free-radical generating compound to form an alkyl-substituted hydroxymethylcyclohexene, alkoxylating this compound to form an alkyl-substituted hydroxypolyalkoxymethylcyclohexene, sulfating the latter compound and neutralizing the sulfate ester with an alkaline material to form the desired product.

7 Claims, No Drawings

PROCESS FOR THE PREPARATION OF ALKALINE SULFATE ESTERS OF N-ALKYL-SUBSTITUTED HYDROXYPOLYALKOXYMETHYLCYCLOHEXENES

CROSS-REFERENCE TO RELATED APPLICATIONS

This application is a continuation-in-part of my copending application Ser. No. 277,835 which was filed on Aug. 3, 1972, now Pat. No. 3,859,324, Jan. 7, 1975, all teachings of which are incorporated herein by reference thereto.

This invention relates to a process for preparing anionic biodegradable detergents. More specifically, the invention is concerned with a novel method comprising a series of steps hereinafter set forth in greater detail whereby alkaline sulfate esters of alkyl-substituted hydroxypolyalkoxymethylcyclohexenes are formed.

One of the major problems which is prevalent in population centers throughout the world is the disposal of sewage containing detergents dissolved therein. Such disposal problems are especially trying in the case of branch-chained alkylaryl detergents. These detergents produce stable foams in hard or soft waters in such large quantities that the foam clogs sewage treatment facilities, and destroys the bacteria which are necessary for proper sewage treatment. In many rivers, streams, lakes, etc., which act as a water supply for the aforesaid population centers, there are found these unwanted foams and suds. As hereinbefore set forth, the presence of these unwanted foams or suds is due in many instances to the use of detergents which are non-biodegradable in nature and which will not break down by bacterial action thereon. The non-biodegradable nature of these detergents is due to the fact that the alkyl side chain of the molecule is in many instances highly branched and therefore not readily attacked by the organisms which would ordinarily destroy the molecule. In contradistinction to this, the use of straight chain alkyl substituents on the ring will permit the detergents to be destroyed and therefore foams or suds will not build up on the surface of the water.

It is therefore an object of this invention to provide a process for the production of detergents which show biodegradability in both urban and rural sewage disposal systems.

In one aspect an embodiment of this invention resides in a process for the preparation of a biodegradable detergent which comprises the steps of: (a) condensing butadiene with allyl alcohol in a Diels-Alder reaction at a temperature in the range of from about 50° to 190° C. and a pressure in the range of from atmospheric to about 100 atmospheres to form hydroxymethylcyclohexene; (b) ring alkylating said hydroxymethylcyclohexene with a 1-alkene in the presence of an organic peroxy free-radical generating compound and hydrogen chloride at a temperature at least as high as the decomposition temperature of said free-radical generating compound; (c) alkoxylating the resultant n-alkyl-substituted hydroxymethylcyclohexene with an alkoxylating agent selected from the group consisting of ethylene oxide and propylene oxide at a temperature in the range of from about 20° to 125° C. and at a pressure of from about 50 to about 1000 pounds per square inch to form an n-alkyl-substituted hydroxypolyalkoxymethylcyclohexene; (d) sulfating said n-alkyl-substituted hydroxypolyalkoxymethylcyclohexene with a sulfating agent at a temperature of from about 0° to about 60° C. to form the sulfate ester thereof; (e) neutralizing said sulfate ester with a neutralizing agent to form the alkaline sulfate ester of said n-alkyl-substituted hydroxypolyalkoxymethylcyclohexene; and (f) recovering said alkaline sulfate ester.

A specific embodiment of this invention is found in a process for the preparation of a biodegradable detergent which comprises the steps of condensing butadiene with allyl alcohol at a temperature in the range of from about 50° to about 190° C and a pressure in the range of from atmospheric to about 100 atmospheres, ring alkylating the resultant hydroxymethylcyclohexene with 1-tetradecene in the presence of di-t-butyl peroxide and hydrogen chloride at a temperature at least as high as the decomposition temperature of said di-t-butyl peroxide, alkoxylating the resultant n-tetradecyl hydroxymethylcyclohexene with ethylene oxide at a temperature in the range of from about 20° to about 125° C. and a pressure in the range of from about 25 to about 1000 pounds per square inch in the presence of an acidic or basic catalyst, sulfating the resultant n-tetradecyl hydroxypolyethoxymethylcyclohexene with sulfuric acid to form the sulfate ester thereof at a temperature in the range of from 0° to about 60° C., neutralizing said sulfate ester with sodium hydroxide at a temperature in the range of from about ambient to about 40° C. and recovering the resultant sodium sulfate ester of an n-tetradecyl hydroxypolyethoxymethylcyclohexene.

Other objects and embodiments will be found in the following further detailed description of the present invention.

As hereinbefore set forth, the present invention is concerned with a process for the preparation of detergents which are biodegradable in nature, said detergents being anionic in nature. The process by which these compounds are formed is effected in a series of steps. In the first step of the reaction, butadiene is condensed with allyl alcohol in a Diels-Alder type condensation to give 4-hydroxymethylcyclohexene. The Diels-Alder condensation is effected at elevated temperatures, usually in the range of from about 50° to about 190° C. and at a pressure ranging from atmospheric to about 100 atmospheres. The reaction pressure may be afforded by the autogenous pressure of butadiene or by a combination of butadiene and a substantially inert gas such as nitrogen or argon, the amount of pressure which is utilized being that which is sufficient to maintain at least a portion of the reactants in the liquid phase.

The 4-hydroxymethylcyclohexene which has been prepared according to the above paragraph is recovered and selectively alkylated utilizing an olefinic hydrocarbon as the alkylating agent. The selective alkylation in which the alkyl substituent is positioned on the ring rather than on the side chain is effected by treating the reactants in the presence of a free-radical generating compound and hydrogen chloride. In the preferred embodiment of the invention, the olefinic hydrocarbon which is utilized as the alkylating agent will comprise a 1-alkene containing from 3 to about 20 carbon atoms in length and preferably from about 6 to about 14 carbon atoms. By utilizing the 1-alkene and an alkylation catalyst comprising a free-radical generating compound and a promoter comprising hydrogen chloride, it is possible to obtain a normal alkyl side chain on the cyclohexene ring rather than a secondary alkyl side chain which would result if the alkylation were effected in the presence of an acidic catalyst of the Friedel-Crafts type or sulfuric acid, etc. Specific examples of the alpha-olefinic hydrocarbons which are utilized as alkylating agents include propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, etc.

The catalysts which are used in this step of the invention will include peroxy compounds, containing the bivalent radical —O—O—, which decomposes to form free radicals which initiate the general reaction and are capable of inducing the condensation of the hydroxymethylcyclohexene with the 1-alkene. Examples of these catalysts include the persulfates, perborates, percarbonates of ammonium and of the alkali metals, or organic peroxy compounds. The organic peroxy compounds constitute a preferred class of catalysts for use in the invention and include peracetic acid, persuccinic acid, methyl ethyl ketone peroxide, methyl isobutyl ketone peroxide, acetyl peroxide, dipropionyl peroxide, di-t-butyl peroxide, butyryl peroxide, lauroyl peroxide, benzoyl peroxide, tetralin peroxide, urea peroxide, t-butyl perbenzoate, t-butyl hydroperoxide, methylcyclohexyl hydroperoxide, cumene hydroperoxide, diisopropylbenzene hydroperoxide, etc. Mixtures of peroxy compound catalysts may be employed or the peroxy compound catalyst may be utilized in admixture with various diluents. Thus, organic peroxy compounds which are compounded commercially with various diluents which may be used include benzoyl peroxide compounded with calcium sulfate, benzoyl peroxide compounded with camphor, phthalate esters, etc. Only catalytic amounts (less than stoichiometric amounts) need be used in the process.

The alkylation of the hydroxymethylcyclohexene with the 1-alkene is effected at elevated reaction temperatures which should be at least as high as the initial decomposition temperature of the free-radical generating catalyst, such as the peroxide compound, in order to liberate and form free radicals which promote the reaction. In selecting a particular reaction temperature for use in the process of the present invention, two considerations must be taken into account. First sufficient energy by means of heat must be supplied to the reaction so that the reactants, namely, the hydroxymethylcyclohexene and the 1-alkenes, will be activated sufficiently for condensation to take place when free radicals are generated by the catalyst. Second, free-radical generating catalysts such as peroxy compounds, particularly organic peroxides, decompose at a measurable rate with time in a logarithmic function dependent upon temperature. This rate of decomposition can be and ordinarily is expressed as the half life of a peroxide at a particular temperature. For example, the half life in hours for di-t-butyl peroxide is 11 hours at 125° C., 4 hours at 135° C., and 1.5 hours at 145° C. A reaction system temperature must then be selected so that the free-radical generating catalyst decomposes smoothly with the generation of free radicals at a half life which is not too long. In other words, sufficient free radicals must be present to induce the present chain reaction to take place, and these radicals must be formed at a temperature at which the reactants are in a suitably activated state for condensation. When the half life of the free-radical generating catalyst is greater than 10 hours, radicals are not generated at a sufficient rate to cause the reaction of the process of the present invention to go forward at a practically useful rate. Thus the reaction temperature may be within the range of from about 50° to about 300° C. and at least as high as the decomposition temperature of the catalyst, by which is meant a temperature such that the half life of the free-radical generating catalyst is not greater than 10 hours. Since the half life for each free-radical generating catalyst is different at different temperatures, the exact temperature to be utilized in a particular reaction will vary. However, persons skilled in the art are well acquainted with the half life vs. temperature data for different free-radical generating catalysts. Thus it is within the skill of one familiar with the art to select the particular temperature needed for any particular catalyst. However, the operating temperatures generally do not exceed the decomposition temperature of the catalyst by more than about 100° C. since free-radical generating catalysts decompose rapidly under such conditions. For example, when a free-radical generating catalyst such as t-butyl perbenzoate is used, having a 10 hour, 50% decomposition temperature of approximately 105° C., the operating temperature of the process is from about 105° to about 205° C. When di-t-butyl peroxide having a decomposition temperature of about 125° C. is used, the process is run at a temperature ranging from about 125° to about 225° C. Higher reaction temperatures may be employed, but little advantage is gained if the temperature is more than the hereinbefore mentioned 100° C. higher than the 10 hour, 50% decomposition temperature of the catalyst. The general effect of increasing the operating temperature is to accelerate the rate of condensation reaction of the hydroxymethylcyclohexene with the 1-alkenes. However, the increased rate of reaction is accompanied by certain amounts of decomposition. In addition to the elevated temperatures which are utilized, the reaction may also be effected at elevated pressures ranging from 1 to about 100 atmospheres or more, the preferred operating pressure of the process being that which is required to maintain a substantial portion of the reactants in liquid phase. Pressure is not an important variable in the process of this invention. However, because of the low boiling points of some of the reactants, it is necessary to utilize pressure-withstanding equipment to insure liquid phase conditions. In batch type operations, it is often desirable to utilize pressure-withstanding equipment to charge the reactants and the catalyst to the vessel and to pressure the vessel with 10 or 30 or 50 or more atmospheres of an inert gas such as nitrogen. This helps to insure the presence of liquid phase conditions. However, when the mole quantity of reactants is sufficient, the pressure which they themselves generate at the temperature utilized is sufficient to maintain the desired phase conditions.

Furthermore, the concentration of the catalyst employed in this process may vary over a rather wide range but it is desirable to utilize low concentrations of catalysts such as from about 0.1 to about 10% of the total weight of the combined starting materials charged to the process. The reaction time may be within the range of from less than 1 minute to several hours, depending upon temperature and the half life of the catalyst. Generally speaking, contact times of at least 10 minutes are preferred.

In addition to the free-radical generating catalyst, the alkylation is also effected in the presence of a hydrogen chloride compound. The hydrogen chloride compound is used as a promoter for the reaction and also is used to prevent or inhibit telomerization, said telomerization being a polymerization reaction in which unwanted side reaction products may be formed. The hydrogen chloride may be present as anhydrous hydrogen chloride, as concentrated hydrochloric acid or as a more dilute aqueous solution of hydrochloric acid, the hydrochloric acid being present in an amount of from 5 to about 38% in said aqueous solution.

The n-alkyl-substituted hydroxymethylcyclohexene is then subjected to an alkoxylation step to prepare a compound having the general structure:

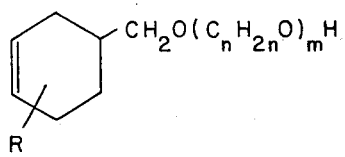

in which R is a normal alkyl radical containing from 3 up to about 20 carbon atoms, $n$ is 2 or 3 and $m$ is an integer ranging from about 1 to about 50 and preferably in a range of from about 3 to about 20. The alkoxylation of the n-alkyl-substituted hydroxymethylcyclohexene is effected by treating the compound with an alkoxylating agent selected from the group consisting of ethylene oxide and propylene oxide in an amount sufficient to produce the desired number of alkoxy units in order that the values hereinbefore set forth for $m$ may be satisfied. In any event, a sufficient amount of alkylene oxide must be used to solubilize the product and maximize its surface active properties either without or with subsequent sulfation. Generally speaking, the value of $m$ will be in the lower range inasmuch as this product is subjected to a subsequent sulfation step to prepare compounds which may be used as an anionic detergent.

The alkoxylation is effected by treating the aforementioned compounds with ethylene oxide or propylene oxide at a temperature in the range of from about 20° (ambient) up to about 125° C. and at a pressure in the range of from about 50 to about 1000 pounds per square inch, the pressure being afforded by the alkoxylating agent. In addition, the alkoxylating reaction is effected in the presence of an acidic or basic catalyst. Examples of acids which may be employed will include mineral acids such as hydrochloric acid, sulfuric acid, phosphoric acid, etc., organic acids such as methanesulfonic acid, ethanesulfonic acid, benzenesulfonic acid, toluenesulfonic acid, acidic salts such as stannic chloride, ferric chloride, zinc chloride, etc. Examples of basic catalysts which may be employed will include sodium carbonate, potassium carbonate, lithium carbonate, sodium acetate, potassium acetate, lithium acetate, sodium propionate, potassium propionate, lithium propionate, sodium hydroxide, potassium hydroxide, lithium hydroxide, the corresponding basic calcium compounds, magnesium compounds, etc. As hereinbefore set forth, a sufficient amount of alkoxylating agent will be used in order that the predetermined value for m in the above formula is satisfied. Therefore, the alkoxylating agent will usually be present in the reaction mixture in a molar excess over that of the n-alkyl-substituted hydroxymethylcyclohexene, said molar excess usually being in a range of from about 2:1 to about 50:1 moles of alkylene oxide per mole of substituted cyclohexene. It is contemplated within the scope of this invention that a fewer number of moles of alkylene oxide may also be used, that is, from about 1 to about 5 moles of alkylene oxide per mole of substituted cyclohexene following which the resulting alkoxylated compound is sulfated and neutralized to form anionic biodegradable detergents of the type

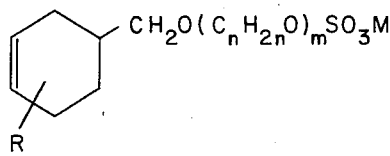

in which R is an n-alkyl radical containing from 3 to about 20 carbon atoms, M is an alkali metal, alkaline earth metal or basic nitrogen-containing ion, $n$ is an integer of 2 or 3 and $m$ is an integer ranging from 1 to about 10. The sulfation of the n-alkyl-substituted hydroxypolyalkoxymethycylohexene is accomplished by treating these compounds with a conventional sulfating agent such as sulfuric acid, oleum, sulfur trioxide, chlorosulfonic acid, etc., the temperatures ranging from about 0° to about 60° C. depending upon the type of sulfating agent which is used. For example, when the sulfating agent comprises sulfur trioxide or oleum, the reaction may be effected at a temperature in the sub-ambient range, that is, from 0° to about 25° C. or if the sulfur trioxide is in gaseous form, the reaction may be effected at a temperature up to about 40° C. When utilizing sulfur trioxide in gaseous form, it is usually admixed with a sufficient amount of air so that the sulfur trioxide is present in an amount in the range of from 3 to about 10%. When employing other sulfating agents such as sulfuric acid, the reaction may be effected over the entire temperature range hereinbefore set forth, that is, from about 0° up to about 60° C. Likewise the use of chlorosulfonic acid as a sulfating agent will permit the reaction to be effected at ambient (20° to 25° C.) temperatures.

The sulfate ester of the n-alkyl-substituted hydroxypolyalkoxymethylcyclohexene is then neutralized by utilizing conventional neutralizing agents such as an alkali metal base, an alkaline earth metal base, ammonia or an amine. Specific examples of these neutralizing agents will include sodium hydroxide, potassium hydroxide, lithium hydroxide, rubidium hydroxide, cesium hydroxide, magnesium hydroxide, calcium hydroxide, strontium hydroxide, ammonia, ammonium hydroxide, amines such as ethanol amine, propanol amine, benzyl amine, N,N-dimethylbenzyl amine, N,N-diethylbenzyl amine, methyl amine, ethyl amine, propyl amine, dimethyl amine, diethyl amine, dipropyl amine, etc. Of the aforementioned neutralizing agents, the preferred compounds comprise ammonium hydroxide, sodium hydroxide, or potassium hydroxide, due to the greater availability and relatively lower cost of these compounds.

The neutralization reaction, being exothermic in nature, is usually effected under a controlled temperature system, the preferred temperature for the reaction being from about ambient up to about 40° C. whereby the formation of undesired side products may be minimized. The control of the temperature of the neutralization reaction is usually effected by utilizing cooling means including ice baths, dry ice, cooling coils, etc., whereby the desired product is obtained.

The process of this invention in which biodegradable detergents of the type hereinbefore set forth in greater detail are prepared may be effected in either a batch or continuous operation. When a batch type operation is used, a quantity of the allyl alcohol is placed in an appropriate apparatus such as an autoclave of the rotating or mixing type. The autoclave is sealed and the butadiene is charged thereto or, in an alternate method, a mixture of butadiene and an inert gas such as nitrogen is charged thereto until the desired operating pressure is reached. The autoclave is thereafter heated to the desired operating temperature within the range hereinbefore set forth and maintained thereat for a predetermined residence time which may range from 0.5 up to about 10 hours or more in duration. Upon completion of the desired residence time, heating is discontinued, the autoclave is allowed to return to room temperature, the excess pressure is vented and the reaction mixture is recovered therefrom. The hydroxymethylcyclohexene is separated from any unreacted allyl alcohol by conventional means such as distillation or by any other separation means known in the art and placed in a second reaction vessel along with a free-radical generating compound and the 1-alkene which is to be utilized as the alkylating agent. This second reaction vessel may be a flask provided with condensing means or an autoclave of the rotating or mixing type. In addition, a promoter comprising hydrogen chloride, either in gaseous form as hydrogen chloride or in aqueous form as hydrochloric acid is added to the reactor which is thereafter heated to the desired operating temperature which, as hereinbefore set forth, is at least as high as the decomposition temperature of said free-radical generating compound. After maintaining the alkylation reaction at this temperature for a predetermined period of time which may range from about 0.5 up to about 10 hours, heating is discontinued, the reaction mixture is allowed to return to room temperature and the n-alkyl-substituted hydroxymethylcyclohexene is separated and recovered by conventional means.

The n-alkyl-substituted hydroxymethylcyclohexene is then treated with an alkoxylating agent to form the desired product. This treatment is accomplished by placing the substituted cyclohexene in an appropriate apparatus such as a rotating autoclave and the alkoxylating agent is added thereto in a predetermined molar excess so that the finished product will contain the requisite number of alkoxy units in the side chain. In addition, an acidic or basic catalyst of the type hereinbefore set forth in greater detail is also added to the apparatus which is thereafter heated to a predetermined operating temperature. After maintaining the apparatus and contents thereof at this temperature for a period of time which may range from about 0.5 up to about 10 hours or more, the apparatus and contents thereof are allowed to return to room temperature and the product is recovered and sent to storage.

Following this, the preparation of the desired anionic detergent of the type hereinbefore set forth in greater detail is effected by treating the n-alkyl-substituted hydroxypolyalkoxymethylcyclohexene with a sulfating agent to form the sulfate ester thereof. This treatment is accomplished by placing the alkene in an appropriate apparatus and adding thereto the sulfating agent. This apparatus may comprise a reaction flask if the sulfating agent, such as sulfuric acid or oleum, is in liquid form, or a pressure vessel if sulfur trioxide in gaseous form is utilized as a sulfating agent. The sulfating reaction is effected at a temperature ranging from 0° to about 60° C., the reactor being cooled or heated according to the particular sulfating agent which is employed, said cooling or heating means which will be employed being of the conventional type such as cooling coils, ice baths, dry ice, or heating coils, etc., if elevated temperatures are employed. The sulfating agent is usually present in a molar excess over the alkene in order to insure complete sulfonation, said molar excess being in a range of from about 0.01:1 to about 1.5:1 moles of sulfating agent per mole of alkene.

The resultant sulfate ester is then neutralized by treatment with a compound of the type hereinbefore set forth. To accomplish this, the sulfate ester is introduced into an appropriate apparatus also provided with cooling means in order to control the temperature of the reaction which, as hereinbefore set forth, is exothermic in nature. The neutralizing agent such as the alkali metal base, alkaline earth metal base, ammonia compound or amine is usually placed in the reactor in a very slight molar excess over the sulfate ester, said slight excess being to insure the complete neutralization of the sulfate ester and the latter is gradually added, with vigorous stirring or agitation. The reaction is allowed to proceed while controlling the temperature thereof, said residence time also being in a range of from about 0.5 up to about 10 hours or more in duration. Upon completion of the desired residence time, the reaction mixture is recovered, and the water removed, whereby the desired alkaline sulfate ester of an n-alkyl-substituted hydroxypolyalkoxymethylcyclohexene is recovered. It is to be understood that for the purposes of this invention the term "alkaline" as used in the present specification and appended claims will include alkali metals, alkaline earth metals, ammonium or amine compounds.

It is also contemplated within the scope of this invention that the desired product may be prepared while employing a continuous manner of operation. When the continuous manner of operation is to be used, the starting materials comprising the allyl alcohol and butadiene are continuously charged to a reactor which is maintained at the proper operating conditions of temperature and pressure. After passage through this reactor for a predetermined period of time, the effluent is continuously withdrawn, subjected to a separation step whereby the unreacted allyl alcohol and butadiene are separated from the hydroxymethylcyclohexene and recycled to form a portion of the feed stock while the latter is continuously charged to an alkylation apparatus which is also maintained at the proper operating conditions of temperature and pressure. In addition, the 1-alkene, the free-radical generating compound and the hydrogen chloride promoter are also continuously charged to the apparatus through separate lines or, if so desired, one or more of the reactants may be admixed with another prior to entry into said reactor and the resulting mixture charged thereto in a single stream. After completion of the desired residence time in the alkylation apparatus, the reactor effluent is continuously withdrawn, again subjected to separation steps whereby unreacted starting materials, promoter and by-products are separated from the alkyl-substituted hydroxymethylcyclohexene. The unreacted starting materials are recycled to the apparatus to form a portion of the feed stock while the n-alkyl-substituted hydroxymethylcyclohexene is continuously charged to the alkoxylation reactor. In this reactor, the aforementioned cyclohexene is subjected to the action of an alkoxylating agent, said agent, either ethylene oxide or propylene oxide, being continuously charged to the reactor in a molar excess over the charge of the cyclohexene. In addition, the catalyst, either acidic or basic in nature, is also charged to the reactor through a separate line or, if so desired, it may be admixed with the carbinol feed and the resulting mixture charged thereto in a single stream. Upon completion of the desired residence time the reactor effluent is withdrawn and, if desired, charged to a sulfating reactor. In this reactor the n-alkyl-substituted hydroxypolyalkoxymethylcyclohexene is subjected to the action of a sulfating agent which is also continuously charged to this reactor, said reactor being maintained at the proper operating conditions, especially temperature. After passage through this reactor for a predetermined period of time, the effluent is continuously withdrawn, again subjected to separation steps whereby undesired impurities are separated from the sulfate ester, and the sulfate ester is continuously charged to the neutralization zone. In this zone, the sulfate ester is subjected to the action of the neutralizing agent which is also continuously charged thereto. Inasmuch as, as hereinbefore set forth, the reaction is exothermic in nature, the temperature of the last named reactor is carefully maintained in a range of from about ambient up to about 40° C. in order that any unwanted side reactions are minimized and a higher yield of the desired product is obtained thereby. As in the prior steps in this continuous type of operation, the reactor effluent is continuously withdrawn and subjected to separation steps whereby the final product may be separated and recovered while any unreacted starting materials are recycled to the neutralization zone to form a portion of the feed stock thereto.

The following examples are given to illustrate the process of the present invention which, however, are not intended to limit the generally broad scope of the present invention in strict accordance therewith.

EXAMPLE I

In this example 58 grams (1.0 mole) of allyl alcohol is placed in the glass liner of a rotating autoclave. The liner is sealed into the autoclave and 54 grams (1.0 mole) of butadiene is charged thereto. The autoclave is then heated to a temperature of 125° C. and maintained thereat for a period of 4 hours, at the end of which time heating is discontinued, and the autoclave is allowed to return to room temperature. The autoclave is opened, the reaction mixture is recovered therefrom and subjected to fractional distillation whereby the desired product comprising 4-hydroxymethylcyclohexene is separated from any unreacted allyl alcohol and recovered.

The 4-hydroxymethylcyclohexene which is prepared according to the above paragraph is then placed in the glass liner of a rotating autoclave along with the alkylating agent comprising 1-octene, the charge stock consisting of a molar excess of the hydroxymethylcyclohexene over the 1-octene in a range of from about 1.5:1 to about 2:1 moles of hydroxymethylcyclohexene per mole of 1-octene. In addition 7 grams of di-t-butyl peroxide and 20 grams of concentrated hydrochloric acid which acts as a promoter are also placed in the autoclave. The liner is sealed into the autoclave and nitrogen is pressed in until an initial operating pressure of 30 atmospheres is reached. Thereafter the autoclave and contents thereof are heated to a temperature of 130° C. and maintained in a range of from 130° to 140° C. for a period of 8 hours. At the end of the 8-hour period, heating is discontinued, the autoclave is allowed to return to room temperature and the excess pressure is discharged therefrom. The autoclave is then opened, the reaction mixture is recovered and subjected to fractional distillation, usually under reduced pressure, whereby the desired product comprising the n-octyl-substituted 4-hydroxymethylcyclohexene is separated from unreacted starting materials, acid, etc., and recovered.

The n-octyl hydroxymethylcyclohexene which has been prepared according to the above paragraphs is then alkoxylated by reaction with ethylene oxide, the mole ratio of ethylene oxide to substituted cyclohexene being 3 moles of ethylene oxide per mole of substituted cyclohexene. The resultant n-octyl hydroxypolyethoxymethylcyclohexene is then placed in a reaction flask and treated with a molar excess of concentrated sulfuric acid, the addition of the acid being carried out at a slow rate during a period of 1 hour. Upon completion of the addition of the sulfuric acid, the mixture is stirred for an additional period of 1 hour, the temperature of the reaction being maintained at room temperature by means of cooling coils. The thus formed sulfate ester of the n-octyl hydroxypolyethoxymethylcyclohexene is then neutralized by treatment with a slight molar excess of sodium hydroxide, said sodium hydroxide being slowly added to the sulfate ester during a period of about 1 hour with continuous stirring and control of the exothermic nature of the reaction by cooling coils. Upon completion of the addition of the sodium hydroxide, the mixture is stirred for an additional 1-hour period and the desired product comprising the sodium sulfate ester of an n-octyl hydroxypolyethoxymethylcyclohexene is recovered.

EXAMPLE II

In a manner similar to that set forth in Example I above, 4-hydroxymethylcyclohexene is prepared by condensing allyl alcohol and butadiene in a Diels-Alder reaction. The thus prepared hydroxymethylcyclohexene is thereafter alkylated by treating a molar excess of the hydroxymethylcyclohexene with 1-tetradecene in the presence of di-t-butyl peroxide and concentrated hydrochloric acid at a temperature in the range of from 130° to 140° C. and a nitrogen pressure of 30 atmospheres for a period of 8 hours. The resulting n-tetradecyl hydroxymethylcyclohexene is then alkylated by reaction with propylene oxide, the mole ratio of propylene oxide to substituted cyclohexene being 3 moles of propylene oxide per mole of cyclohexene. As in Example I above, the resultant n-tetradecyl hydroxypolypropoxymethylcyclohexene is placed in a reaction flask and treated with a molar excess of concentrated sulfuric acid. Upon completion of the addition, which is accomplished during a period of 1 hour, the mixture is stirred for an additional 1 hour while maintaining the temperature of the reaction at room temperature by means of cooling coils. Following this, the sulfate ester of the n-tetradecyl hydroxypolypropoxymethylcyclohexene is neutralized in a treatment step using a slight molar excess of sodium hydroxide, the sodium hydroxide being slowly added to the ester during a period of 1 hour accompanied by cntinuous stirring and a control of the exothermic nature of the reaction by means of cooling coils. The mixture, after completion of the addition of the sodium hydroxide, is stirred for an additional period of 1 hour and the desired product comprising the sodium sulfate ester of an n-tetradecyl hydroxypolypropoxymethylcyclohexene is separated and recovered.

EXAMPLE III

To a reactor containing 6 grams of benzoyl peroxide and 20 grams of concentrated hydrochloric acid is added a mixture of 4-hydroxymethylcyclohexene and 1-decene, the substituted cyclohexene being in a molar excess over the 1-decene. The reactor is sealed and heated to a temperature of 80° C., being maintained in a range of from 80° to 90° C. for a period of 8 hours. At the end of this time, heating is discontinued and the reactor is allowed to return to room temperature. The n-decyl hydroxymethylcyclohexene is separated and recovered from any unreacted starting materials and thereafter is alkoxylated by reaction with ethylene oxide in a manner similar to that set forth in Example I above, the mole ratio of ethylene oxide to substituted cyclohexene being 3moles of ethylene oxide per mole of substituted cyclohexene.

To form the desired anionic biodegradable detergent, the n-decyl hydroxypolyethoxymethylcyclohexene is placed in a reaction flask and treated with a molar excess of oleum, the acid being slowly added during a period of 1 hour to the hexene while maintaining the temperature of the reaction in a subambient range by means of cooling coils. Upon completion of the addition of the oleum, the mixture is stirred for an additional period of 1 hour and the thus formed sulfate ester is neutralized by treatment with a slight molar excess of potassium hydroxide. The potassium hydroxide solution is slowly added to the sulfate ester during a period of 1 hour while continuously stirring the mixture and controlling the exothermic nature of the reaction by external cooling coils. Upon completion of the addition of the potassium hydroxide solution, the mixture is stirred for an additional period of 1 hour following which the desired product comprising the potassium hydroxide sulfate ester of an n-decyl hydroxypolyethoxymethylcyclohexene is separated and recovered.

EXAMPLE IV

To prepare a desired anionic biodegradable detergent, 4-hydroxymethylcyclohexene which is prepared according to the method set forth in Example I above is treated in a similar manner by alkylating said substituted cyclohexene with 1-tridecene utilizing a catalyst comprising di-t-butyl peroxide and a promoter comprising concentrated hydrochloric acid in an autoclave under 30 atmospheres of nitrogen and a reaction temperature in the range of from 130° to 140° C. for a period of 1 hour. The n-tridecyl hydroxymethylcyclohexene which is prepared according to this method, after recovery from the reaction mixture, is alkoxylated by treatment with 3 moles of propylene oxide per mole of substituted cyclohexene, the alkoxylation step being effected in an autoclave in the presence of a catalytic amount of sodium carbonate, the autoclave being heated to a temperature of 50° C. and being maintained thereat for a period of 4 hours. Upon completion of the 4-hour period, the autoclave is allowed to return to room temperature, the excess pressure is discharged and the n-tridecyl hydroxypolypropoxymethylcyclohexene is recovered. This product is then placed in an autoclave provided with cooling means and a molar excess of sulfur trioxide is charged thereto. Upon completion of the addition of the sulfur trioxide, the mixture is again stirred for an additional period of 1 hour and neutralized by the addition of a sodium hydroxide solution, the addition of the sodium hydroxide accompanied by stirring and cooling of the reaction mixture during a 1 hour period. Upon completion of the addition of the sodium hydroxide and after an additional period of 1 hour during which the reaction mixture is continuously stirred, the desired product comprising the sodium sulfate ester of n-tridecyl hydroxypolypropoxymethylcyclohexene is separated and recovered.

EXAMPLE V

In this example 4-hydroxymethylcyclohexene which is prepared in a manner similar to that set forth in the above examples is ring alkylated by treating said cyclohexene with 1-dodecene in a rotating autoclave in the presence of a di-t-butyl peroxide catalyst and a promoter comprising hydrogen chloride under an applied pressure of 30 atmospheres of nitrogen at a temperature ranging from 130° to 140° C. for a period of 8 hours. At the end of the 8-hour period, heating of the autoclave is discontinued, the autoclave is allowed to return to room temperature and the excess pressure is discharged therefrom. The autoclave is opened, the reaction mixture is recovered and subjected to fractional distillation under reduced pressure whereby the product comprising n-dodecyl hydroxymethylcyclohexene is recovered.

The alkyl-substituted cyclohexene is then placed in the glass liner of a rotating autoclave and a catalytic amount of sodium carbonate is added thereto. The autoclave is sealed and 3 moles of ethylene oxide per mole of cyclohexene is charged thereto, following which the autoclave is heated to a temperature of 50° C. and maintained thereat for a period of 4 hours. At the end of this time, heating is discontinued, the excess pressure is discharged and the autoclave is opened. After subjecting the mixture to fractional distillation under reduced pressure, the resultant n-dodecyl hydroxypolyethoxymethylcyclohexene is recovered.

The substituted cyclohexene prepared according to the above paragraph is then placed in a reaction flask which is provided with external cooling means. A molar excess of chlorosulfonic acid is slowly added thereto during a period of 1 hour accompanied by continuous stirring of the reaction mixture and maintenance of the temperature in a range of from 25° to 25° C. Upon completion of the addition of the chlorosulfonic acid, the mixture is stirred for an additional period of 1 hour and thereafter neutralized by the addition of a potassium hydroxide solution. The addition of the potassium hydroxide solution is accompanied by continuous stirring and maintenance of the exothermic nature of the reaction at subambient temperatures ranging from about 15° to 20° C. by the external cooling means. After completion of the addition of the potassium hydroxide solution, the mixture is stirred for an additional period of 1 hour and the desired anionic biodegradable detergent comprising the potassium sulfate ester of an n-dodecyl hydroxypolyethoxymethylcyclohexene is separated and recovered.

I claim as my invention:

1. A process for the preparation of a biodegradable detergent which comprises the steps of:

a. condensing butadiene with allyl alcohol in a Diels-Alder reaction at a temperature in the range of from about 50° to 190° C. and a pressure in the range of from atmospheric to about 100 atmospheres to form hydroxymethylcyclohexene;

b. ring alkylating said hydroxymethylcyclohexene with a 3 to 20 carbon atom 1-alkene in the presence of an organic peroxy free-radical generating compound and hydrogen chloride at a temperature at least as high as the decomposition temperature of said free-radical generating compound;

c. alkoxylating the resultant n-alkyl-substituted hydroxymethylcyclohexene with an alkoxylating agent selected from the group consisting of ethylene oxide and propylene oxide at a temperature in the range of from about 20° to 125° C. and at a pressure of from about 50 to about 1000 pounds per square inch to form an n-alkyl-substituted hydroxypolyalkoxymethylcyclohexene;

d. sulfating said n-alkyl-substituted hydroxypolyalkoxymethylcyclohexene with a sulfating agent at a temperature of from about 0° to about 60° C. to form the sulfate ester thereof;

e. neutralizing said sulfate ester with a neutralizing agent to form the alkaline sulfate ester of said n-alkyl-substituted hydroxypolyalkoxymethylcyclohexene; and f. recovering said alkaline sulfate ester.

2. The process as set forth in claim 1 in which said peroxy compound is di-t-butyl peroxide or benzoyl peroxide, said sulfating agent is selected from the group consisting of sulfuric acid, sulfur trioxide and chlorosulfonic acid, and said neutralizing agent is an alkali.

3. The process as set forth in claim 1 in which said 1-alkene is 1-octene, said alkoxylating agent is ethylene oxide, said sulfating agent is sulfuric acid, said neutralizing agent is sodium hydroxide and said alkaline sulfate ester of an n-alkyl-substituted hydroxypolyalkoxymethylcyclohexene is the sodium sulfate ester of an n-octyl hydroxypolyethoxymethylcyclohexene.

4. The process as set forth in claim 1 in which said 1-alkene is 1-tetradecene, said alkoxylating agent is propylene oxide, said sulfating agent is sulfuric acid, said neutralizing agent is sodium hydroxide and said alkaline sulfate ester of an n-alkyl-substituted hydroxypolyalkoxymethylcyclohexene is the sodium sulfate ester of an n-tetradecyl hydroxypolypropoxymethylcyclohexene.

5. The process as set forth in claim 1 in which said 1-alkene is 1-decene, said alkoxylating agent is ethylene oxide, said sulfating agent is oleum, said neutralizing agent is potassium hydroxide and said alkaline sulfate ester of an n-alkyl-substituted hydroxypolyalkoxymethylcyclohexene is the potassium sulfate ester of an n-decyl hydroxypolyethoxymethylcyclohexene.

6. The process as set forth in claim 1 in which said 1-alkene is 1-tridecene, said alkoxylating agent is propylene oxide, said sulfating agent is sulfur trioxide, said neutralizing agent is sodium hydroxide and said alkaline sulfate ester of an n-alkyl-substituted hydroxypolyalkoxymethylcyclohexene is the sodium sulfate ester of an n-tridecyl hydroxypolypropoxymethylcyclohexene.

7. The process as set forth in claim 1 in which said 1-alkene is 1-dodecene, said alkoxylating agent is ethylene oxide, said sulfating agent is chlorosulfonic acid, said neutralizing agent is potassium hydroxide, and said alkaline sulfate ester of an n-alkyl-substituted hydroxypolyalkoxymethylcyclohexene is the potassium sulfate ester of an n-dodecyl hydroxypolyethoxymethylcyclohexene.

* * * * *